US00PP35855P2

(12) United States Plant Patent
Van Swieten

(10) Patent No.: US PP35,855 P2
(45) Date of Patent: Jun. 4, 2024

(54) ***PHALAENOPSIS* ORCHID PLANT NAMED 'PHA525998'**

(50) Latin Name: ***Phalaenopsis* hybrid**
Varietal Denomination: PHA525998

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,592

(22) Filed: Nov. 6, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHA525998', particularly characterized by having medium-size, purple, striped flowers with red-purple lips, leaf apex is acute, leaf attitude is semi-erect to horizontal, and incurving longitudinal axis, and is propagated by meristem tissue culture, is disclosed.

3 Drawing Sheets

Genus and species: *Phalaenopsis* hybrid.
Variety denomination: 'PHA525998'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA525998'.

The new *Phalaenopsis* plant is a product of a planned breeding program conducted by the inventor in Bleiswijk, the Netherlands. The objective of this breeding program was to create a new *Phalaenopsis* plant with medium-size, purple, striped flowers with red-purple lips suitable for potted plant production.

The new *Phalaenopsis* plant 'PHA525998' is a result of cross-pollination made by the inventor in April 2013 in Bleiswijk, the Netherlands, of the proprietary female, or seed parent, *Phalaenopsis* hybrid '00001-3358' (unpatented) with the proprietary male, or pollen parent, *Phalaenopsis* hybrid '00001-4627' (unpatented).

The new *Phalaenopsis* was selected by the inventor as a single plant within the progeny of the stated cross-pollination in a controlled greenhouse in Bleiswijk, the Netherlands, in April 2017. Asexual reproduction of the new *Phalaenopsis* plant by meristem tissue culture since 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 20, 2022 (Application no. 2022/1063), by Applicant who obtained the subject matter disclosed directly from the inventor. 'PHA525998' has not been made publicly available or sold anywhere in the world prior to the effective filing date of this application with the exception of sales or disclosures made one year or less before the effective filing date of this claimed invention by Applicant who obtained 'PHA525998' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA525998' as a new and distinct variety of *Phalaenopsis* plant:

1) purple, striped flowers with red-purple lips;
2) leaf shape of apex is acute;
3) leaf attitude is semi-erect to horizontal; and
4) dorsal sepal: curvature of longitudinal axis is incurving.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 42-week-old plants in August 2023. Colors in the photographs may differ from the color values cited in the detailed botanical description, which accurately describe the actual colors of the new variety.

DESCRIPTION OF THE NEW VARIETY

Figure 1:
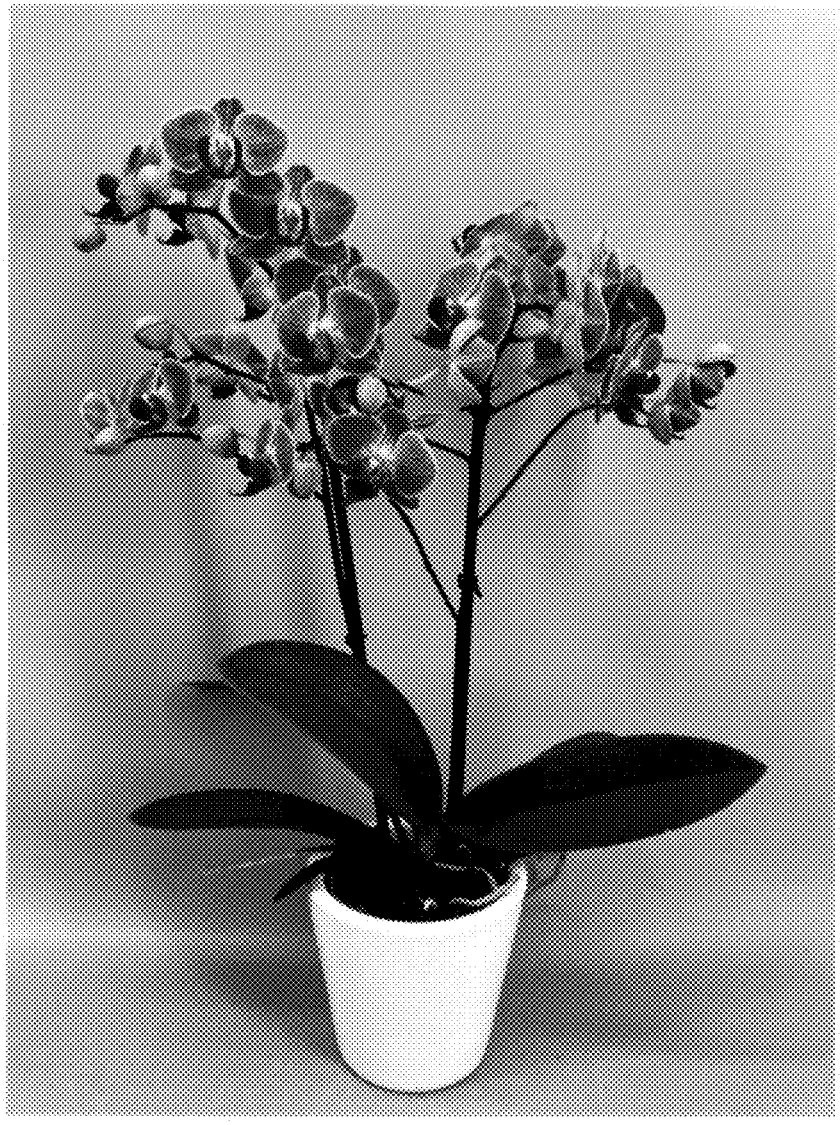
FIG. 1 shows the overall plant habit, including blooms, buds, and foliage of 'PHA525998'.
Figure 2:
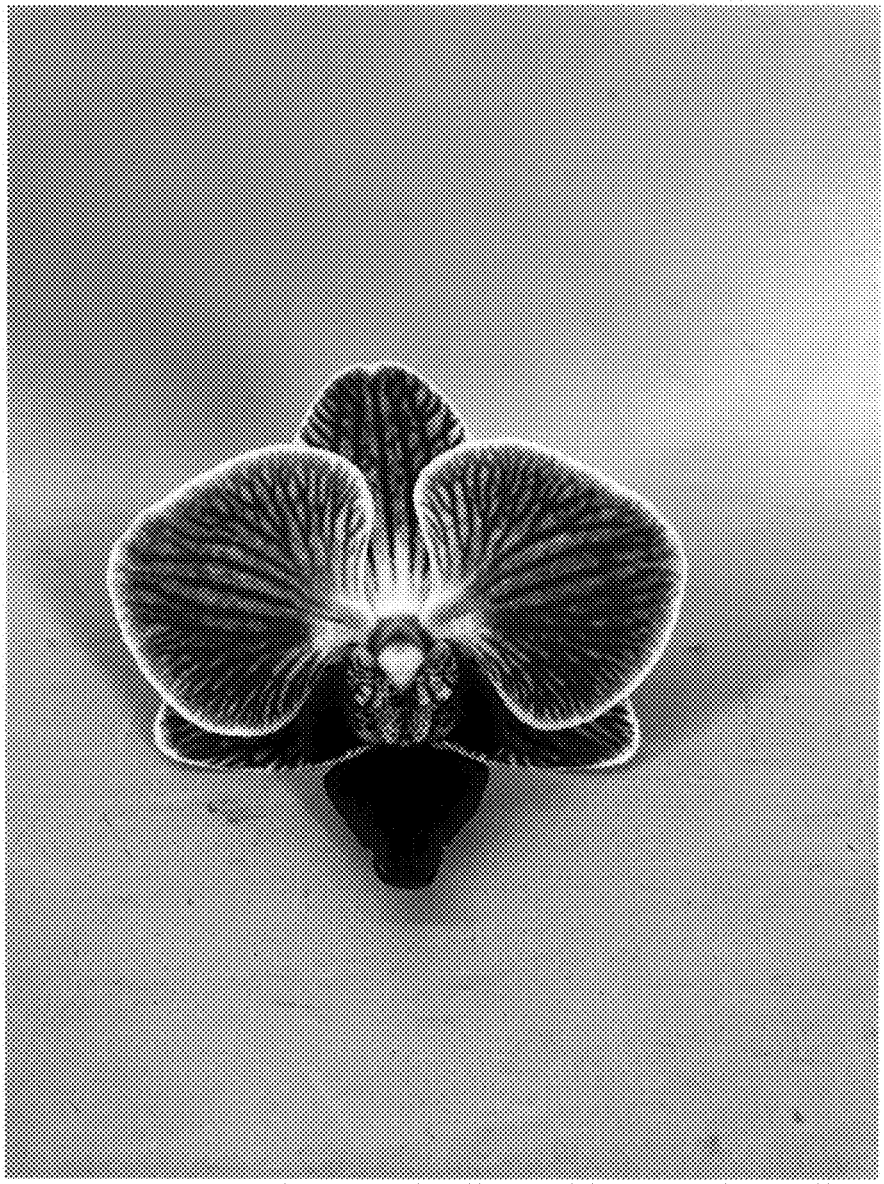
FIG. 2 shows a close-up of a flower of 'PHA525998'.
Figure 3:
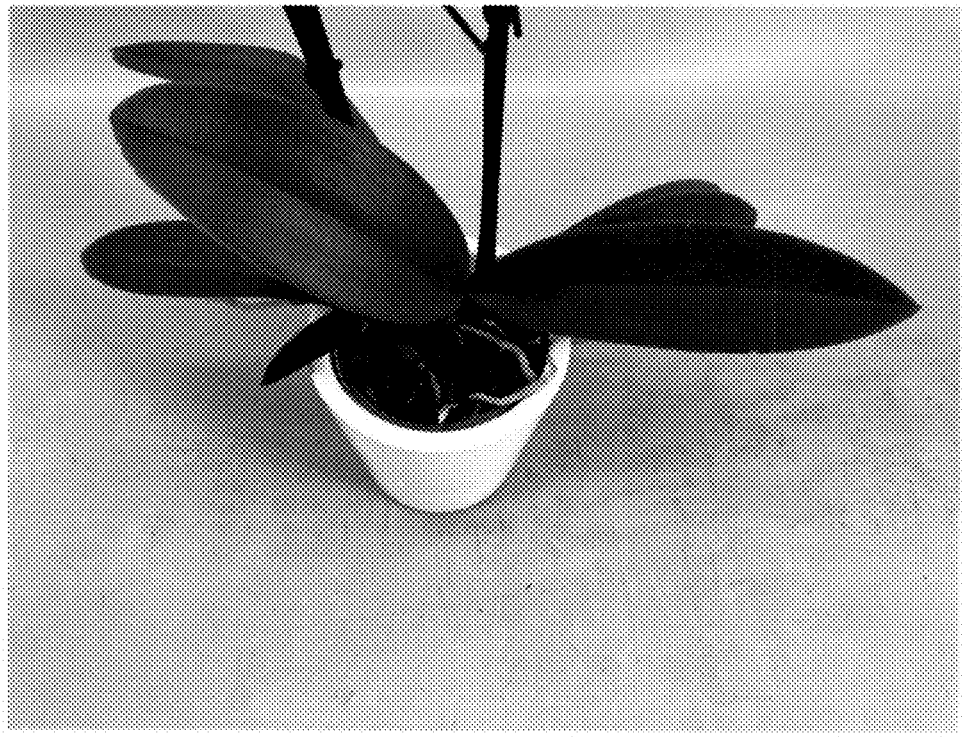
FIG. 3 shows an overhead, close-up view of the leaves of 'PHA525998'.

The following detailed description sets forth the distinctive characteristics of 'PHA525998'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in August 2023 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA525998'.

Parentage:

*Female parent*.—*Phalaenopsis* cultivar '00001-3358' (unpatented).

*Male parent*.—*Phalaenopsis* cultivar '00001-4627' (unpatented).

Propagation:

*Type*.—Meristem tissue culture.

Roots:

*Root description*.—Greyed-green colored roots (a color in between RHS 190B and RHS 190C) with branching lateral roots having yellow-green (RHS 144C) with yellowish-green colored root tips (RHS N144A).

Plant:

*Crop time to flowering*.—Following asexual propagation (in vitro), the rooted cuttings grow for 18-20 weeks. After transplantation into 9-cm pots, the plants are finished after 40 to 42 weeks.

*Growth habit of the peduncle*.—Upright to slightly pendent with panicle inflorescence.

*Height* (*from soil level to top of inflorescence*).—Approximately 37.0 cm to 42.0 cm.

*Width* (*measured from leaf tips*).—About 34.0 cm to 37.0 cm.

*Vigor*.—Strong.

Leaves:

*Mature leaves*.—Quantity per plant: 8 to 9 leaves are produced before flowering. Length (fully expanded): 17.0 cm to 19.0 cm. Width: 4.5 cm to 5.5 cm. Position of the broadest part of the leaf: At the middle. Shape: Oblong. Base shape: Moderately elongated. Apex: Moderately asymmetric acute. Leaf blade angle with the petiole (measured from the horizontal position): Between 10 degrees and 25 degrees. Leaf margin: Entire. Color: Upper surface: Green (RHS 146A). Lower surface: Green (RHS 146B). Texture (both upper and lower surfaces): Smooth. Thickness: 1.7 mm to 2.0 mm. Variegation: Absent. Venation: Pattern: Parallel. Color of the midvein: Upper surface: Green (RHS 147A). Lower surface: Green (RHS 146B).

Peduncle:

*Quantity per plant*.—2.

*Number of flowers per peduncle*.—17 to 22.

*Length*.—37.0 cm to 42.0 cm.

*Diameter*.—2.0 mm to 3.0 mm.

*Strength*.—Strong.

*Aspect*.—Upright to slightly pendent.

*Texture*.—Smooth.

*Color*.—Brown (RHS 200B) with a touch of green (RHS 146D).

*Internode length*.—2.0 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—2.

*Inflorescence size*.—Height (from base to tip): 220.0 mm to 270.0 mm.

*Flowering time*.—First flowers can be expected 7 to 8 months after planting in a 9-cm pot.

*Flower*.—Height: 45.0 mm to 50.0 mm. Diameter: 55.0 mm to 60.0 mm. Depth of lip: 20.0 mm to 22.0 mm.

*Flower shape*.—Flat.

*Flower longevity*.—On the plant: 12 to 14 weeks.

*Fragrance*.—Absent.

*Flower bud*.—Average size: Medium. Length: 16.0 mm to 18.0 mm. Width: 13.0 mm to 15.0 mm. Shape: Egg shaped. Color: Light yellow-green (a color in between RHS 145B and RHS 145C) with reddish-purple stripes (RHS N78B).

*Petals*.—Arrangement: Open/free. Shape: Medium. Apex: Obtuse asymmetric. Margin: Weakly undulated. Length (from base to tip): 26.0 mm to 28.0 mm. Width: 31.0 mm to 33.0 mm. Position of the broadest part of the petal: Toward the base. Color (when fully opened): Upper surface: Basic color: White (RHS NN155C). Over color: Purple shade (RHS N80B); reddish-purple stripes and netting (RHS N78A). Lower surface: Basic color: RHS NN155D. Over color: Light purple shade (RHS N80C); reddish-purple stripes (RHS N78B). Number of spots, dots, and stripes on the petals (upper surface): Many stripes. Color of spots, dots, and stripes on the petals (upper surface): RHS N78A. Density of netting of the petals (upper surface): Low. Color of the netting (upper surface): RHS N78A.

*Dorsal sepal*.—Shape: Elliptic. Apex: Emarginated symmetric. Margin: Entire. Length (from base to tip): 29.0 mm to 31.0 mm. Width: 20.0 mm to 22.0 mm. Position of the broadest part of the dorsal sepals: At the middle. Color (when fully opened): Upper surface: Basic color: White (RHS NN155C). Over color: Purple shade (RHS N80B); purple stripes and netting (RHS N80A). Lower surface: Basic color: White (RHS NN155D). Over color: Very light purple shade (RHS 76B); diluting purple stripes (RHS N80B). Number of spots, dots, and stripes on the dorsal sepals (upper surface): Medium stripes. Color of spots, dots, and stripes on the dorsal sepals (upper surface): RHS N80A. Density of netting of the dorsal sepals (upper surface): Medium. Color of the netting (upper surface): RHS N80A.

*Lateral sepals*.—Shape: Ovate. Apex: Obtuse asymmetric. Margin: Entire. Length (from base to tip): 29.0 mm to 31.0 mm. Width: 19.0 mm to 21.0 mm. Position of the broadest part of the lateral sepals: At the base. Color (when fully opened): Upper surface: Basic color: White (RHS NN155C). Over color: Touch of light green (RHS 145D) and dotted RHS 60C at the base; purple shade (RHS N80B); purple stripes and netting (RHS N80A). Lower surface: Basic color: White (RHS NN155D). Over color: Touch of light green (RHS 145D) at the base; light purple shade (RHS 76C) and diluting light purple stripes (RHS N80C). Number of spots, dots, and stripes on the lateral sepals (upper surface): Medium stripes and medium number of very small dots at the base. Color of spots, dots, and stripes on the lateral sepals (upper surface): Stripes RHS N80A; dots RHS 60C. Density of netting of the lateral sepals (upper surface): Low. Color of the netting (upper surface): RHS N80A.

*Labellum* (*lip*).—Whiskers: Present. Length of whiskers: 5.0 mm to 6.0 mm. Color of whiskers: Reddish-purple (RHS N78A) with small light greenish-yellow tips (RHS 8C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 16.0 mm to 18.0 mm. Width: 9.0 mm to 11.0 mm. Color: Upper surface: A touch of yellow (RHS 13A) and white (RHS 158D) with stripes RHS 59A) at the base; purplish-red (RHS 59B) and reddish-purple (RHS N78A) toward the tip. Lower surface: White (RHS NN155D) on one side from the base; touch of purplish-red (RHS 59B) toward margin on the other side and reddish-purple (RHS N78A) toward the tip . Number of spots and stripes on the lateral lobe: Few stripes at the base. Color of spots and stripes on the lateral lobe: RHS 59B. Density of netting of the lateral lobe: None. Color of the netting: Not applicable.

*Apical lobe*.—Shape: Triangular. Margin: Entire. Length: 18.0 mm to 20.0 mm. Width: 17.0 mm to 19.0 mm. Color: Upper surface: Purplish-red (RHS 59B) at the base; reddish-purple (RHS N78A) toward whiskers. Lower surface: Light purple (RHS 76A) at the middle from base toward whiskers; purplish-red (RHS 59B) toward wings; reddish-purple (RHS N78A) toward margins and whiskers. Number of spots and stripes on the apical lobe: None. Color of spots and stripes on the apical lobe: Not applicable. Density of netting of the apical lobe: None. Color of the netting: Not applicable.

*Callus*.—Average size: Small. Height: 4.0 mm to 5.0 mm. Length: 5.0 mm to 6.0 mm. Width: 3.0 mm to 4.0 mm. Color: Yellow (RHS 13A) with purplish-red (RHS 59B) dots.

Reproductive organs:

*Column*.—Length: 9.0 mm to 10.0 mm. Diameter: 4.0 mm to 5.0 mm. Color: Light purple (RHS N75C) at the base and reddish-purple (RHS N78B) toward the tip.

*Pollinia*.—Quantity: 2. Diameter: 0.8 mm to 1.0 mm.. Color: Orange-yellow (RHS 23A).

*Ovary*.—Length: 7.0 mm to 10.0 mm. Diameter: 1.7 mm to 1.9 mm.

*Pedicel*.—Length: 33.0 mm to 35.0 mm. Diameter: 2.0 mm to 2.3 mm. Color: Light yellow-green (a color in between RHS 145B and RHS 145C) at the base; light green (RHS 157C) with a hint of very light purple (RHS 76C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA525998' differs from the female parent plant '00001-3358' (unpatented) in that 'PHA525998' has white petals, and the main color of the callus is yellow, whereas '00001-3358' has purplish-pink petals, and the main color of the callus is light yellow-green.

'PHA525998' differs from the male parent plant '00001-4627' (unpatented) in that 'PHA525998' has a yellow callus, acute leaves, and no flecks on the petals, whereas '00001-4627' has a dark red callus, obtuse leaves, and few to medium flecks on the petals.

'PHA525998' is most similar to the commercial *Phalaenopsis* plants named 'PHALDONFI' (U.S. Plant Pat. No. 26,066) and 'PHALFROFE' (U.S. Plant Pat. No. 31,979). 'PHA525998' differs from the commercial variety 'PHALDONFI' in that 'PHA525998' has more narrow leaves, semi-erect to horizontal leaf attitude, and acute apex, whereas 'PHALDONFI' has wider leaves, erect leaf attitude, and obtuse to acute apex.

'PHA525998' differs from the commercial variety 'PHALFROFE' in that 'PHA525998' has white petals with low density of netting, more narrow leaves that are moderately elongated, whereas 'PHALFROFE' has very light purple petals with high density of netting, wider leaves that are slightly elongated.

I claim:

1. A new and distinct variety of *Phalaenopsis* plant named 'PHA525998', substantially as described and illustrated herein.

* * * * *